(12) United States Patent
Tadano et al.

(10) Patent No.: US 12,390,238 B2
(45) Date of Patent: Aug. 19, 2025

(54) SURGICAL DEVICE

(71) Applicant: RIVERFIELD INC., Tokyo (JP)

(72) Inventors: Kotaro Tadano, Tokyo (JP); Koki Shindo, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 510 days.

(21) Appl. No.: 17/849,018

(22) Filed: Jun. 24, 2022

(65) Prior Publication Data
US 2022/0313296 A1 Oct. 6, 2022

Related U.S. Application Data

(63) Continuation of application No. PCT/JP2019/051045, filed on Dec. 25, 2019.

(51) Int. Cl.
*A61B 17/28* (2006.01)

(52) U.S. Cl.
CPC .............................. *A61B 17/2804* (2013.01)

(58) Field of Classification Search
CPC ..... A61B 17/2804; A61B 34/71; A61B 34/70; A61B 2034/305; A61B 2034/306; A61B 2034/715; A61B 2017/2927; A61B 2017/2929; A61B 2017/2939
See application file for complete search history.

(56) References Cited

U.S. PATENT DOCUMENTS

| | | | |
|---|---|---|---|
| 5,797,900 A * | 8/1998 | Madhani | A61B 34/30 606/1 |
| 11,058,503 B2 * | 7/2021 | Chassot | A61B 34/71 |
| 2003/0036748 A1 | 2/2003 | Cooper et al. | |
| 2009/0112230 A1 | 4/2009 | Jinno | |
| 2015/0150635 A1 | 6/2015 | Kilroy et al. | |
| 2016/0135914 A1 | 5/2016 | Isoda | |
| 2017/0252096 A1 | 9/2017 | Felder et al. | |
| 2018/0000543 A1 * | 1/2018 | Hibner | A61B 34/20 |
| 2019/0125463 A1 * | 5/2019 | Hunter | A61B 34/71 |
| 2019/0159853 A1 * | 5/2019 | Haraguchi | A61B 34/70 |
| 2019/0274769 A1 * | 9/2019 | Perdue | A61B 34/35 |

(Continued)

FOREIGN PATENT DOCUMENTS

| | | |
|---|---|---|
| JP | 2009-107087 A | 5/2009 |
| JP | 2011-072574 A | 4/2011 |

(Continued)

OTHER PUBLICATIONS

International Search Report for PCT/JP2019/051045 dated Feb. 25, 2020.

(Continued)

*Primary Examiner* — Shaun L David
*Assistant Examiner* — Rachael L Geiger
(74) *Attorney, Agent, or Firm* — Sughrue Mion, PLLC

(57) ABSTRACT

A surgical device includes a forceps device that performs a bending movement and opening and closing movements of grasping portions of the forceps device, driven portions to which a driving force is transmitted from outside the surgical device, and plural cords, each being fixed to one of the driven portions, the cords transmitting movements of the driven portions to the forceps device. The forceps device performs one or both of the bending movement and the opening and closing movements when all or a portion of the cords are pulled.

14 Claims, 11 Drawing Sheets

(56) References Cited

U.S. PATENT DOCUMENTS

2019/0328467 A1 10/2019 Waterbury et al.
2023/0329807 A1* 10/2023 Heye ..................... A61B 34/37

FOREIGN PATENT DOCUMENTS

| JP | 4938753 B2 | 5/2012 |
| JP | 2016-518160 A | 6/2016 |
| WO | 2015/012023 A1 | 1/2015 |
| WO | 2018/179140 A1 | 10/2018 |
| WO | 2019/006087 A2 | 1/2019 |

OTHER PUBLICATIONS

Office Action dated Oct. 26, 2022 from the European Patent Office in EP Application No. 19957760.2.

* cited by examiner

SURGICAL DEVICE

CROSS REFERENCE TO RELATED APPLICATIONS

This application is a continuation application of International Patent Application No. PCT/JP2019/051045, filed on Dec. 25, 2019, which is incorporated by reference herein in its entirety.

BACKGROUND

1. Field

The present disclosure relates to a surgical device.

2. Description of Related Art

For master-slave surgical robots, there have been demands for a technology for transmitting external forces acting on robotic forceps (surgical device) to an operator who operates the robot from an isolated place in order to improve safety and reduce the time for doctors to learn the operation. An external force transmitted to the operator is estimated on the basis of information such as the position and the driving force of an actuator, etc.

A related art method of transmitting driving force generated by a driving source such as an actuator via wires to a surgical device to drive the surgical device tends to have a complicated mechanism.

SUMMARY

It is an aspect to provide a novel structure that relatively simply drives a surgical device.

According to an aspect of one or more embodiments, a surgical device may include a forceps device configured to perform a bending movement and to perform opening and closing movements of grasping portions of the forceps device; a plurality of driven portions to which a driving force is transmitted from outside the surgical device; and a plurality of cords, each being fixed to one of the plurality of driven portions, the plurality of cords transmitting movements of the plurality of driven portions to the forceps device, wherein the forceps device performs at least one of the bending movement and the opening and closing movements when at least a portion of the plurality of cords are pulled.

According to another aspect of one or more embodiments, a surgical device may include a forceps device; a plurality of driven portions to which a driving force is transmitted from outside the surgical device; and a plurality of cords, each being fixed to one of the plurality of driven portions, the plurality of cords transmitting movements of the plurality of driven portions to the forceps device. The forceps device may include a first arm; a second arm connected to the first arm by a first joint that is rotatable about a first axis by a first one of the plurality of cords; and a plurality of grasping portions connected to the second arm by a second joint that is rotatable about a second axis by respective second ones of the plurality of cords, the second axis being different from the first axis, and the first joint and the second joint are rotatable independently of each other.

DETAILED DESCRIPTION

In a related art method for driving a surgical device of a robot, a method of transmitting driving force generated by a driving source such as an actuator via wires to a surgical device, wires are arranged between the driving source and the surgical device, and are adjusted to have a tension within a predetermined range. However, this method for driving the surgical device decelerates the rotating force of a motor via some gears and then drives the surgical device, which makes the mechanism complicated.

Figure 1:
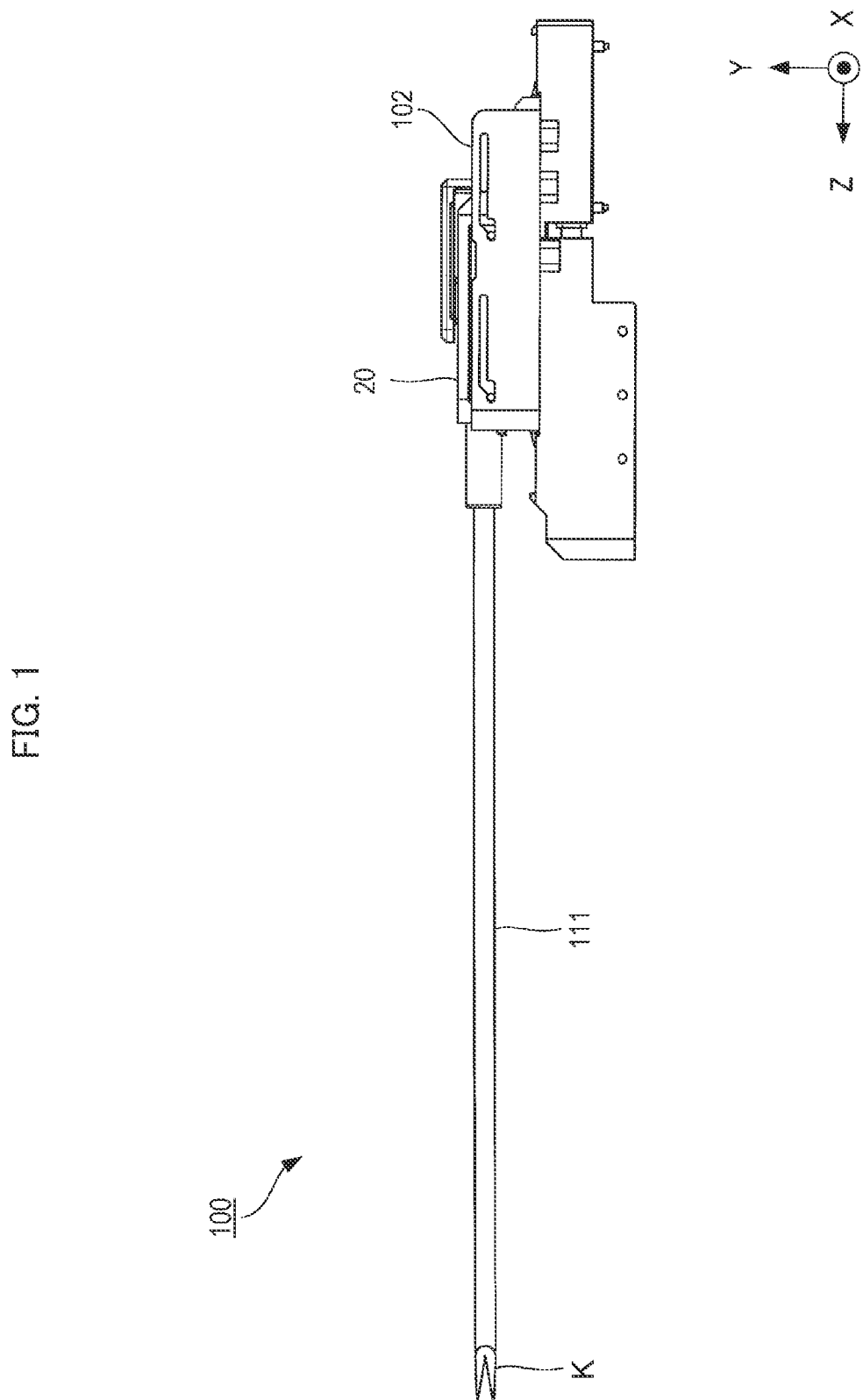
FIG. 1 is a drawing for explaining a structure of a surgical device according to an embodiment.
Figure 2:
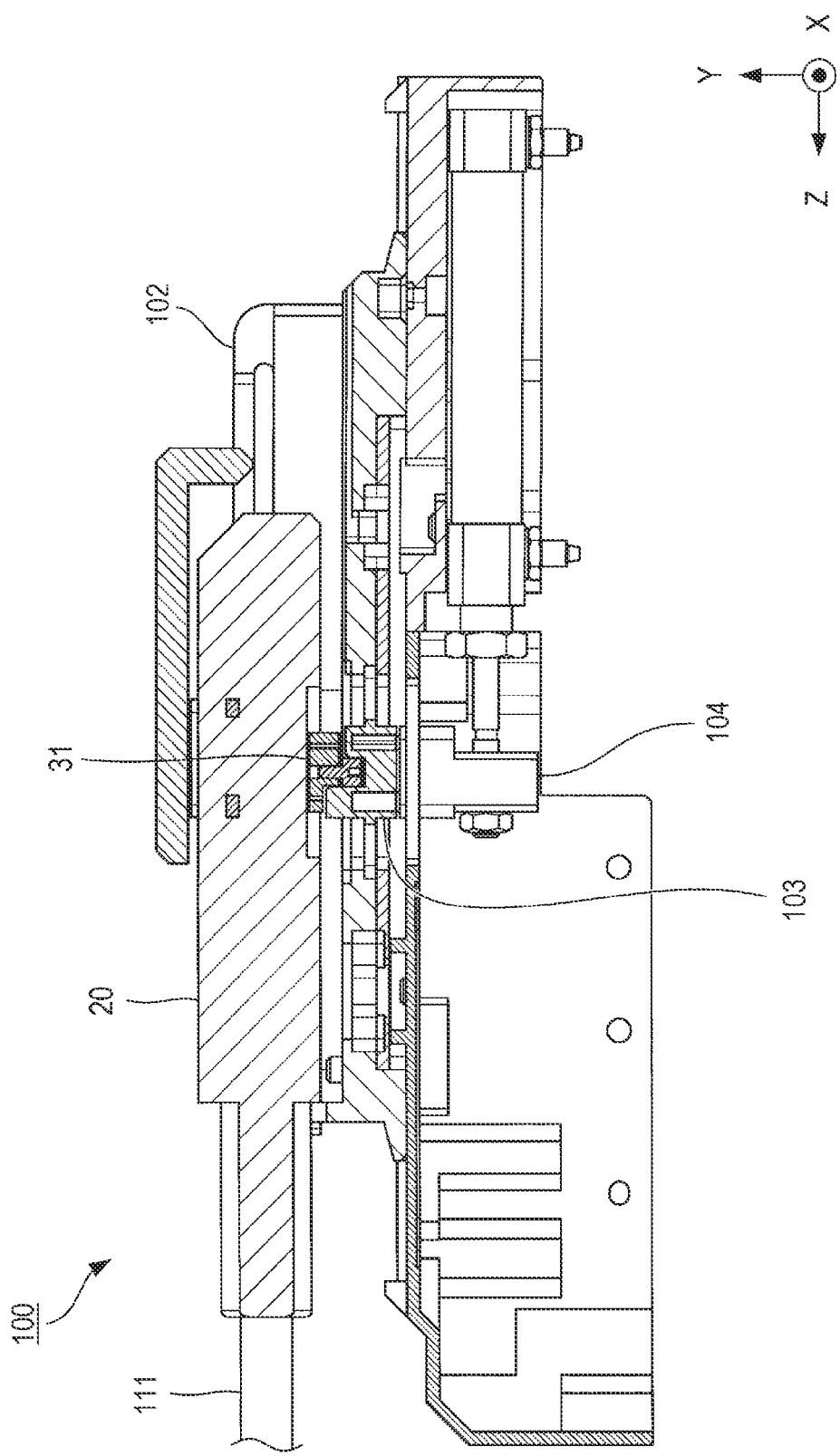
FIG. 2 is a partial cross-sectional view explaining an engaged state of the surgical device in FIG. 1 with an adapter, according to an embodiment.
Figure 3:
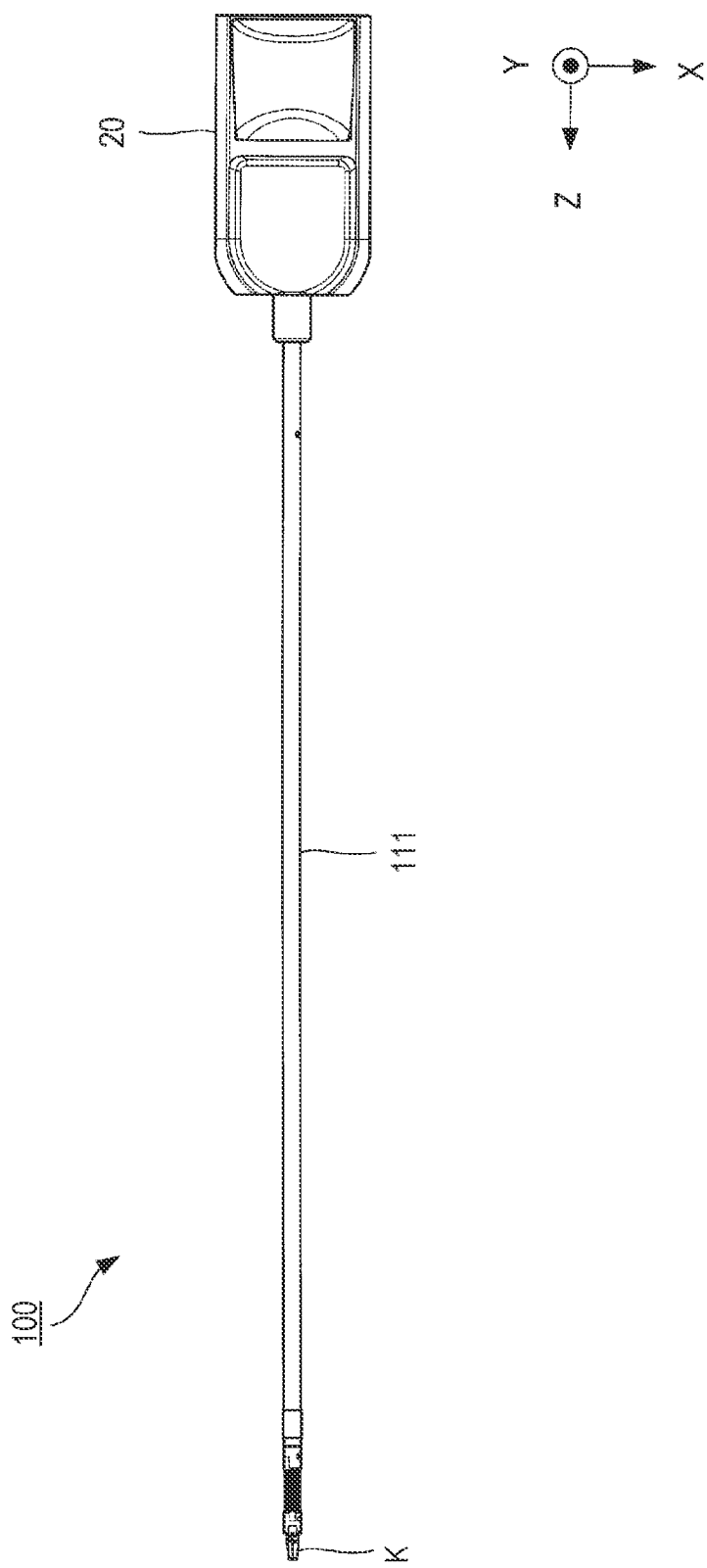
FIG. 3 is a perspective view explaining arrangement of a first housing part and a second housing part of the surgical device in FIG. 1, according to an embodiment.
Figure 4:
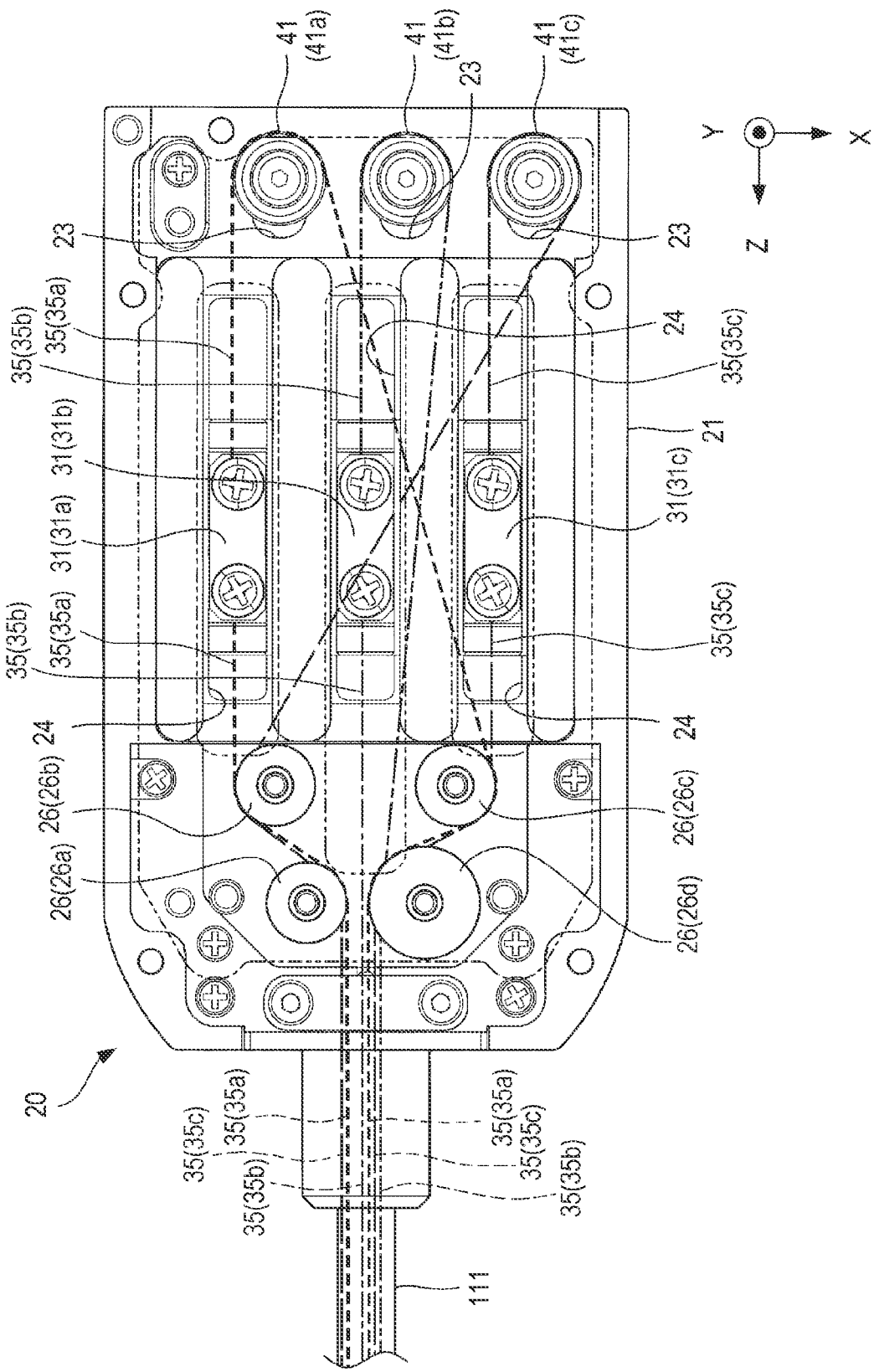
FIG. 4 is a top view explaining a structure inside a housing in FIG. 1, according to an embodiment.
Figure 5:
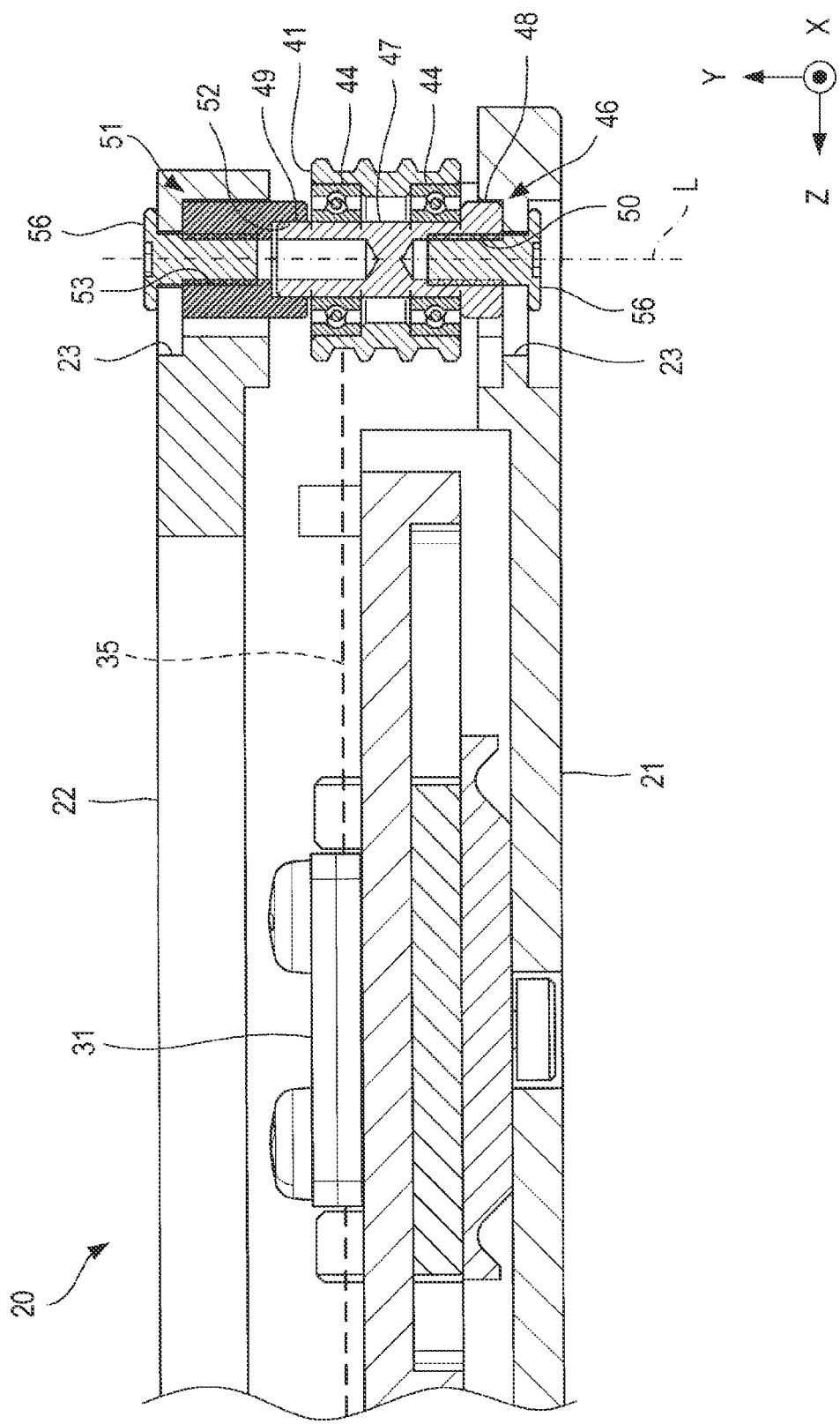
FIG. 5 is a partial cross-sectional view explaining the structure inside the housing in FIG. 1, according to an embodiment.

A surgical device 100 according to an embodiment will be described with reference to FIGS. 1 to 5. FIG. 1 is a drawing for explaining a structure of the surgical device according to an embodiment. FIG. 2 is a partial cross-sectional view explaining an engaged state of the surgical device FIG. 1 with an adapter, according to an embodiment. FIG. 3 is a perspective view explaining arrangement of a first housing part and a second housing part of the surgical device in FIG. 1, according to an embodiment. FIG. 4 is a top view explaining a structure inside a housing in FIG. 1, according to an embodiment. FIG. 5 is a partial cross-sectional view explaining the structure inside the housing in FIG. 1, according to an embodiment.

The surgical device 100 of an embodiment is to be applied to a master-slave surgical robot and to be used in operations. As described in FIG. 1, the surgical device 100 mainly includes a shaft 111 having a leading end at which forceps (operating part) K are located, and a housing 20 to be mounted on a surgical robot.

The shaft 111 is a member formed in a rod-like shape extending from the housing 20. An embodiment is described referring to application to an example in which the shaft 111 is a rod-shaped member extending in a Z-axis direction. A forceps device K, which is the operating part, is provided on the leading end, which is an end opposite the housing 20 (an end on a positive side of the Z axis), of the shaft 111. A space extending from the housing 20 to the forceps device K (along the Z-axis direction) is formed inside the shaft 111. A plurality of wires 35, which will be described later, may be arranged in the space.

As illustrated in FIG. 2, the housing 20 is attachable to and detachable from an adapter 102 of a surgical robot. Driving force for driving the forceps device K is transmitted from a power unit 104 to the housing 20 via a power transmission part (external) 103 of the adapter 102.

As illustrated in FIGS. 3 to 5, the housing 20 mainly includes a first housing part (support part) 21, a second housing part (support part) 22, drive elements (driven portions) 31, the wires (cords) 35, pulleys (rotating members) 41, pulley rotating shafts (rotating shaft parts) 46, fixing blocks (fixing parts) 51, and fixing screws (fixing elements) 56.

As illustrated in FIGS. 4 and 5, the first housing part 21 and the second housing part 22 are plate-shaped members constituting at least part of the body of the housing 20. An embodiment will be described referring to application to an example in which the first housing part 21 is located on a side of the housing 20 facing the adapter 102 (a face on the Y axis negative side of the housing 20), and the second housing part 22 is located on a side of the housing 20 opposite the adapter 102 (a face on the Y axis positive side of the housing 20). In addition, an embodiment is described referring to application to an example in which the first housing part 21 and the second housing part 22 are parallel to the X-Z plane.

As illustrated in FIGS. 4 and 5, at least the wires 35, guide pulleys 26, the pulleys 41, the pulley rotating shafts 46, and the fixing blocks 51 are arranged between the first housing part 21 and the second housing part 22.

In regions near the ends of the first housing part 21 and the second housing part 22 on a side opposite the shaft 111 (on the Z axis negative side), long holes 23 for pulley used for arrangement of the pulleys 41 are formed.

The long holes 23 for pulley are through-holes extending toward the shaft 111 side (the Z axis positive side) of the first housing part 21 and the second housing part 22. In other words, the long holes 23 for pulley are long holes extending along the Z-axis direction. An embodiment is described referring to application to an example in which three long holes 23 for pulley are arranged in the X-axis direction with a space therebetween. Alternatively, the number of long holes 23 for pulley may be more than or less than three.

The first housing part 21 has long holes 24 for driving in which the drive elements 31 are disposed. The long holes 24 for driving allow movement of the drive elements 31 in a direction along the first housing part 21, and restrict movement thereof in a direction away from the first housing part 21 (the Y-axis direction).

The long holes 24 for driving are located at positions on the first housing part 21 closer to the shaft 111 than the long holes 23 for pulley are. For example, the long holes 24 for driving are located in a central region in the Z-axis direction of the first housing part 21.

The long holes 24 for driving are through-holes extending linearly toward the shaft 111 side (the Z axis positive side). In other words, the long holes 24 for driving are long holes extending along the Z-axis direction. An embodiment is described referring to application to an example in which three long holes 24 for driving are arranged in the X-axis direction with a space therebetween. Alternatively, the number of long holes 24 for driving may corresponds to the number of long holes 23 for pulley, and may be more than or less than three.

An embodiment is described referring to application to an example in which three long holes 24 for driving have an equal length in the Z-axis direction. Note that the lengths in the Z-axis direction of the three long holes 24 for driving may be equal to each other as mentioned above, or may be different from each other.

The guide pulleys 26 guide the wires 35, which extend from the drive elements 31 to the shaft 111, into an internal space of the shaft 111. More specifically, the guide pulleys 26 guide the wires 35, which extend from the drive elements 31 each located on the positive side or the negative side in the X-axis direction with respect to the shaft 111 with a space from the shaft 111, to the shaft 111.

As illustrated in FIGS. 4 and 5, the guide pulleys 26 are arranged in an end region on the shaft 111 side (on the Z axis positive side) between the first housing part 21 and the second housing part 22. In other words, the guide pulleys 26 are arranged between the long holes 24 for driving and the shaft 111 in a space between the first housing part 21 and the second housing part 22.

The guide pulleys 26 are attached to at least one of the first housing part 21 and the second housing part 22, and are each rotatable about an axis along the Y-axis direction. The shapes and structures of the guide pulleys 26 may be known shapes and structures, which are not particularly limited.

As illustrated in FIGS. 4 and 5, the drive elements 31 receives driving force transmitted from the power transmission part 103 of the adapter 102, and transmit the transmitted driving force to the wires 35. The drive elements 31 are caused to reciprocate along the long holes 24 for driving by the driving force transmitted from the power transmission part 103.

The face of each drive element 31 facing the long hole 24 for driving has a projecting and recessed shape that allows relative movement of the element 31 along the first housing part 21 and restricts movement thereof away from the first housing part 21. Each long hole 24 for driving has a projecting and recessed shape to be engaged with the projecting and recessed shape of the drive element 31. Note that the projecting and recessed shapes may be known shapes, and are not particularly limited.

Furthermore, a region of each drive element 31 facing the power transmission part 103 has a projecting and recessed shape used for transmission of the driving force. The projecting and recessed shape is a shape allowing the drive elements 31 and the power transmission part 103 to be engaged with and separated from each other in the Y-axis direction. Note that the projecting and recessed shape may be a known shape, and is not particularly limited.

The wires 35 transmit the driving force transmitted to the drive elements 31 to the forceps device K. In other words, the wires 35 transmit the movement of the drive elements 31 to the forceps device K. Known materials and shapes may be used for the material and the shape of the wires 35, and are not particularly limited.

A wire 35 that extends from a drive element 31 in the Z-axis negative direction is wound around a pulley 41. After being wound around the pulley 41, the wire 35 extends in the Z-axis positive direction and is guided into the shaft 111.

A wire 35 that extends in the Z-axis positive direction from a drive element 31 that is located away from the shaft 111 in the X-axis direction, for example, is wound around a guide pulley 26 and guided into the shaft 111.

The wires 35 that are guided into the shaft 111 transmit the driving force to the forceps device K. The structure for transmitting the driving force may be a known structure. For example, the end of each of the wires 35 guided into the shaft 111 may be attached to the forceps device K, or the ends of the respective wires 35 may be connected in a loop shape and wound around a pulley in the forceps device K.

The connection between forceps and each wire will be described with reference to a forceps device, which will be describe later.

The pulleys 41 are members formed in a cylindrical shape having a circumferential face around which a wire 35 is wound. Each pulley 41 changes the direction of a wire 35 extending from a drive element 31 in the Z-axis negative direction to the Z-axis positive direction.

Each of the pulleys 41 is arranged in a long hole 23 for pulley with a pulley rotating shaft 46, a fixing block 51, and a fixing screw 56. In other words, the pulleys 41 are positioned so that the drive elements 31 are between the shaft 111 on which the forceps device K is provided and the pulleys 41.

Each of the cylindrical pulleys 41 has a length in the central axis direction, that is, a height in the Y-axis direction shorter (lower) than the distance between the first housing part 21 and the second housing part 22.

The internal space of each cylindrical pulley 41 is a space in which the pulley rotating shaft 46 is located, and bearings 44 that support the pulley 41 so that the pulley 41 is rotatable about the rotation axis L are disposed between the pulley 41 and the pulley rotating shaft 46. Note that the central axis of the pulley 41 is coincident with the rotation axis L.

The circumferential face of each cylindrical pulley 41 has three annular grooves arranged at regular intervals in the central axis direction of the pulley 41 (the Y-axis direction). The embodiment illustrated in FIGS. 4-5 is described referring to application to an example in which the grooves have a width equal to a length corresponding to the width of two wires 35 arranged adjacent to each other. Alternatively, the width of each of the grooves may be larger or smaller than the width of two wires 35 arranged adjacent to each other.

Each of the pulleys 41 further has two cutouts connecting adjacent grooves. The cutouts are formed by cutting off portions of ridge-like projections defining adjacent grooves, and each have a width allowing a wire 35 to extend from one groove to another. The embodiment illustrated in FIGS. 4-5 is described referring to application to an example in which two cutouts are arranged at the same phase on the circumferential face of the pulley 41. Note that the two cutouts may be arranged at the same phase, or may be arranged at different phases from each other.

As illustrated in FIG. 5, the pulley rotating shafts 46 are each a member formed in a cylindrical or columnar shape that rotatably supports the pulley 41. Each of the pulley rotating shafts 46 mainly includes an insertion portion 47 inserted through the bearings 44 disposed in the internal space of the pulley 41, and an enlarged diameter portion 48 disposed at one end of the insertion portion 47. A leading end (projecting portion) 49 of the insertion portion 47 is to be inserted in a recessed portion 52 of a fixing block 51, which will be described later.

The enlarged diameter portion 48 has a shape with a diameter larger than the inner diameter of the bearings 44 through which the insertion portion 47 is inserted. The pulley rotating shafts 46 each have a length with which an end of the insertion portion 47 and an end of the enlarged diameter portion 48 stick out from the pulley 41 in a state in which the insertion portion 47 is inserted through the bearings 44 and the enlarged diameter portion 48 is in contact with one of the bearings 44.

An end of each pulley rotating shaft 46 has a screw hole 50, which is to be engaged with the fixing screw 56, on an end face thereof adjacent to the enlarged diameter portion 48. The screw hole 50 is located on the central axis of the cylindrical or columnar pulley rotating shaft 46. Note that the screw hole 50 may be a hole extending through the pulley rotating shaft 46 or may be a bottomed hole.

The fixing blocks 51 are each a member formed in a cylindrical or columnar shape that supports the pulley rotating shaft 46 and the pulley 41. The end of each fixing block 51 adjacent to the pulley rotating shaft 46 has the recessed portion 52 in which the leading end 49 of the insertion portion 47 is inserted, and the opposite end of the fixing block 51 has a screw hole 53 to be engaged with the fixing screw 56.

While the embodiment illustrated in FIG. 5 is described referring to application to an example in which the recessed portion 52 is formed on the fixing block 51 and the leading end 49 of the insertion portion 47 is inserted in the recessed portion 52, alternatively, a recessed portion may be formed on the insertion portion 47 and a projecting portion formed on the fixing blocks 51 may be inserted in the recessed portion.

The fixing block 51 is located between the leading end 49 of the pulley rotating shaft 46 and the second housing part 22. The fixing block 51 may move in the Z-axis direction relative to the second housing part 22, and may be fixed. In addition, the position of the fixing block 51 relative to the pulley rotating shaft 46 may be changed along the Y-axis direction, and the movement of the fixing block 51 in the X-axis direction and the Z-axis direction relative to the pulley rotating shaft 46 is restricted.

As illustrated in FIG. 5, the fixing screw 56 is an external thread inserted in the long hole 23 for pulley, and screwed with the pulley rotating shaft 46 and the fixing block 51. The first housing part 21 is sandwiched between the fixing screw 56 screwed in the screw hole 50 of the pulley rotating shaft 46 and the pulley rotating shaft 46, and the fixing screw 56 presses the pulley rotating shaft 46 against the first housing part 21 and thus fixes the pulley rotating shaft 46. The second housing part 22 is sandwiched between the fixing screw 56 screwed in the screw hole 53 of the fixing block 51 and the fixing block 51, and the fixing screw 56 presses the fixing block 51 against second housing part 22 and thus fixes the fixing block 51.

Next, the operation of the surgical device 100 having the structure described above will be explained. As illustrated in FIG. 2, the driving force for driving the forceps device K of the surgical device 100 is transmitted from the power unit 104 to the drive elements 31 via the power transmission part 103 of the adapter 102. As illustrated in FIGS. 2 and 4, the drive elements 31 reciprocate along the long holes 24 for driving in the Z-axis direction relative to the housing 20.

The movement of the drive elements 31 is transmitted to the wires 35. Each wire 35 reciprocates along a direction in which the wire 35 extends. A wire 35 that extends from a drive element 31 toward the forceps device K (on the positive side of the Z-axis direction) reciprocates along the directions in which the wire 35 is guided by a guide pulley 26. A wire 35 that extends from a drive element 31 toward a pulley 41 (on the negative side in the Z-axis direction) reciprocates along the directions in which the wire 35 is guided by a pulley 41 and a guide pulley 26.

The wires 35 extend through the internal space of the shaft 111 to the forceps device K, and the reciprocating movements of the wires 35 are transmitted to the forceps device K. The forceps device K performs opening and closing movements on the basis of the reciprocating movements of the wires 35. While the embodiment illustrated in FIGS. 4-5 is described referring to application to an example in which the forceps device K performs opening and closing operations on the basis of the reciprocating movements of the wires 35, the forceps device K may also perform other movements such as a bending movement for changing the orientation thereof.

In the embodiment illustrated in FIGS. 4-5, three wires (three braided wires) are provided to achieve two bending movements and one opening and closing (pinching) movement of the forceps. The layout of the wires in the housing will now be described.

A wire 35a has one end or a portion fixed to one side, closer to the forceps device K, of a drive element 31a, and the other end or another portion fixed to the other side, closer to the pulleys 41, of the drive element 31a. The wire 35a extending from the side, closer to the forceps device K, of the drive element 31a is passed over guide pulleys 26a and 26b, and guided to the internal space of the shaft 111. In addition, the wire 35a extending from the side, closer to the pulleys 41, of the drive element 31a is passed over a pulley 41a and guide pulleys 26c and 26d, and guided to the internal space of shaft 111.

A wire 35b has one end or a portion fixed to one side, closer to the forceps device K, of a drive element 31b, and the other end or another portion fixed to the other side, closer to the pulleys 41, of the drive element 31b. The wire 35b extending from the side, closer to the forceps device K, of the drive element 31b is guided directly to the internal space of shaft 111. In addition, the wire 35b extending from the side, closer to the pulleys 41, of the drive element 31b is passed over a pulley 41b and the guide pulley 26d, and guided to the internal space of shaft 111.

A wire 35c has one end or a portion fixed to one side, closer to the forceps device K, of a drive element 31c, and the other end or another portion fixed to the other side, closer to the pulleys 41, of the drive element 31c. The wire 35c extending from the side, closer to the forceps device K, of the drive element 31c is passed over the guide pulleys 26c and 26d, and guided to the internal space of shaft 111. In addition, the wire 35c extending from the side, closer to the pulleys 41, of the drive element 31c is passed over a pulley 41c and the guide pulleys 26a and 26b, and guided to the internal space of shaft 111.

Note that each of the pulleys illustrated in FIG. 4 is actually one of a plurality of pulleys, which overlap each other in the drawing, having a common axis. The wires are passed over different pulleys that overlap each other. In other words, no more than one wire may be passed over each groove of the pulleys.

Forceps Device

Next, the forceps device according to an embodiment will be described in detail with reference to the drawings where appropriate.

The embodiment illustrated in FIGS. 1-5 relates to a forceps device including wire-driven forceps of a surgical robot. Specifically, the embodiment illustrated in FIGS. 1-5 relates to a wire guide structure of a forceps manipulator having multi-degree-of-freedom bendable joints. Note that forceps are one of surgical instruments used for pinching tissue, a foreign substance, or the like.

Note that, in order to avoid interference between joints, a wire for driving a leading end joint needs to pass the rotation center of a joint located on a base side thereof. In addition, a bending point of the wire needs to bend in such a manner as to fold with zero curvature. This is because passing the rotation center and bending in a folding manner enable the wire to have a constant path length regardless of the bending angle of the joint.

In addition, in order to restrict the wire path without increasing sliding friction of a wire at a joint, the radius of curvature of a wire guide needs to be increased or a guide roller is needed. Because the radius of curvature of a wire guide or the radius of a guide roller has a finite value, the wire bends in such a manner as to curve along the radius of the wire guide or the guide roller, and thus cannot bend in such a manner as to fold with zero curvature. Thus, a change in the path length cannot actually be completely avoided. Various embodiments described herein, however, propose a mechanism that minimizes the change in the path length.

The forceps device according to an embodiment includes a roller base (guide base) supporting a guide roller (wire guide) that guides a wire to or near a bendable joint portion. The roller base is rotatable independently of components, such as an arm and joints, constituting the forceps device. This minimizes interference between wires when being bent in a case where a plurality of wires are controlled by guide rollers.

Figure 6:
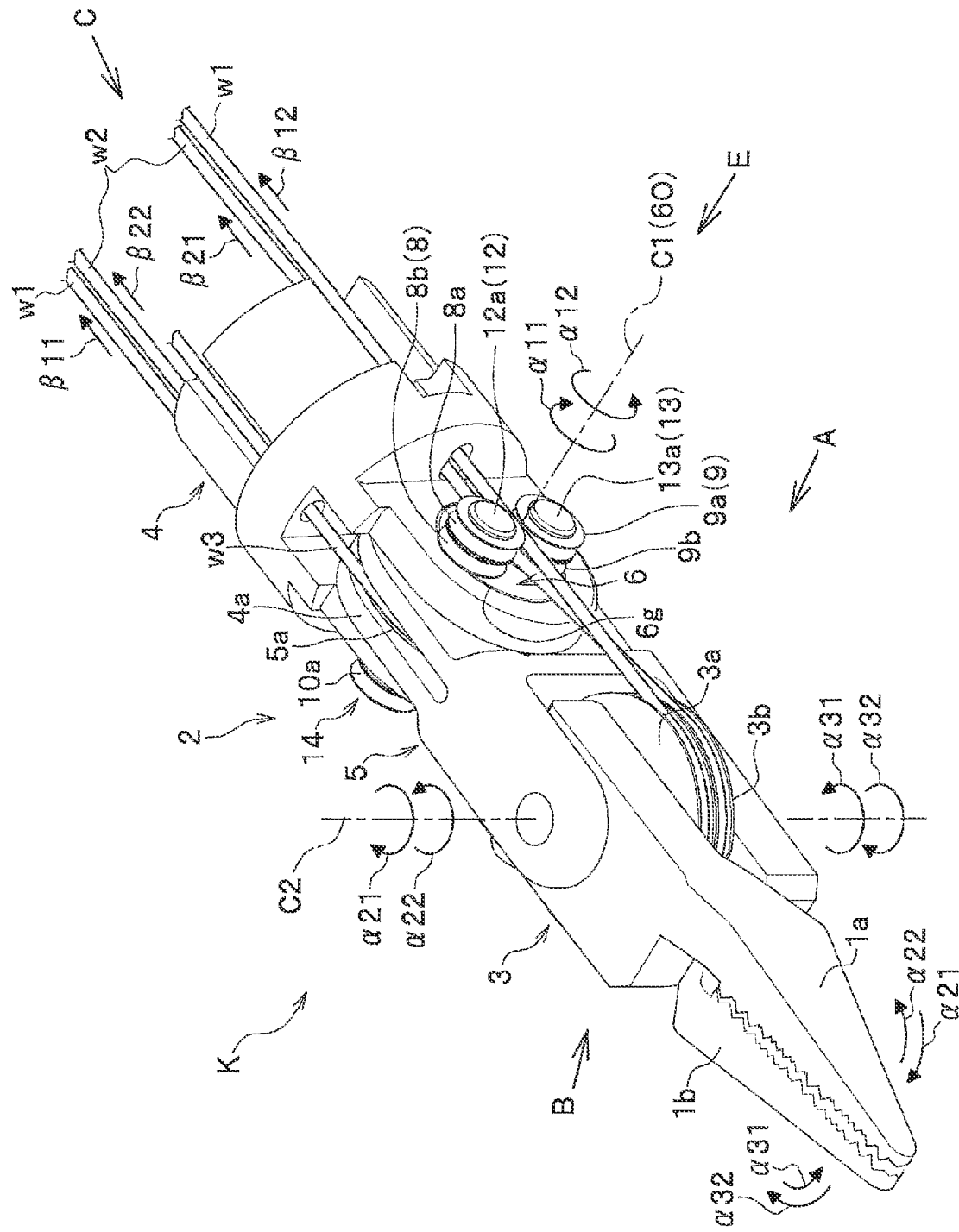
FIG. 6 is a perspective view of a forceps device, according to an embodiment.
Figure 7:
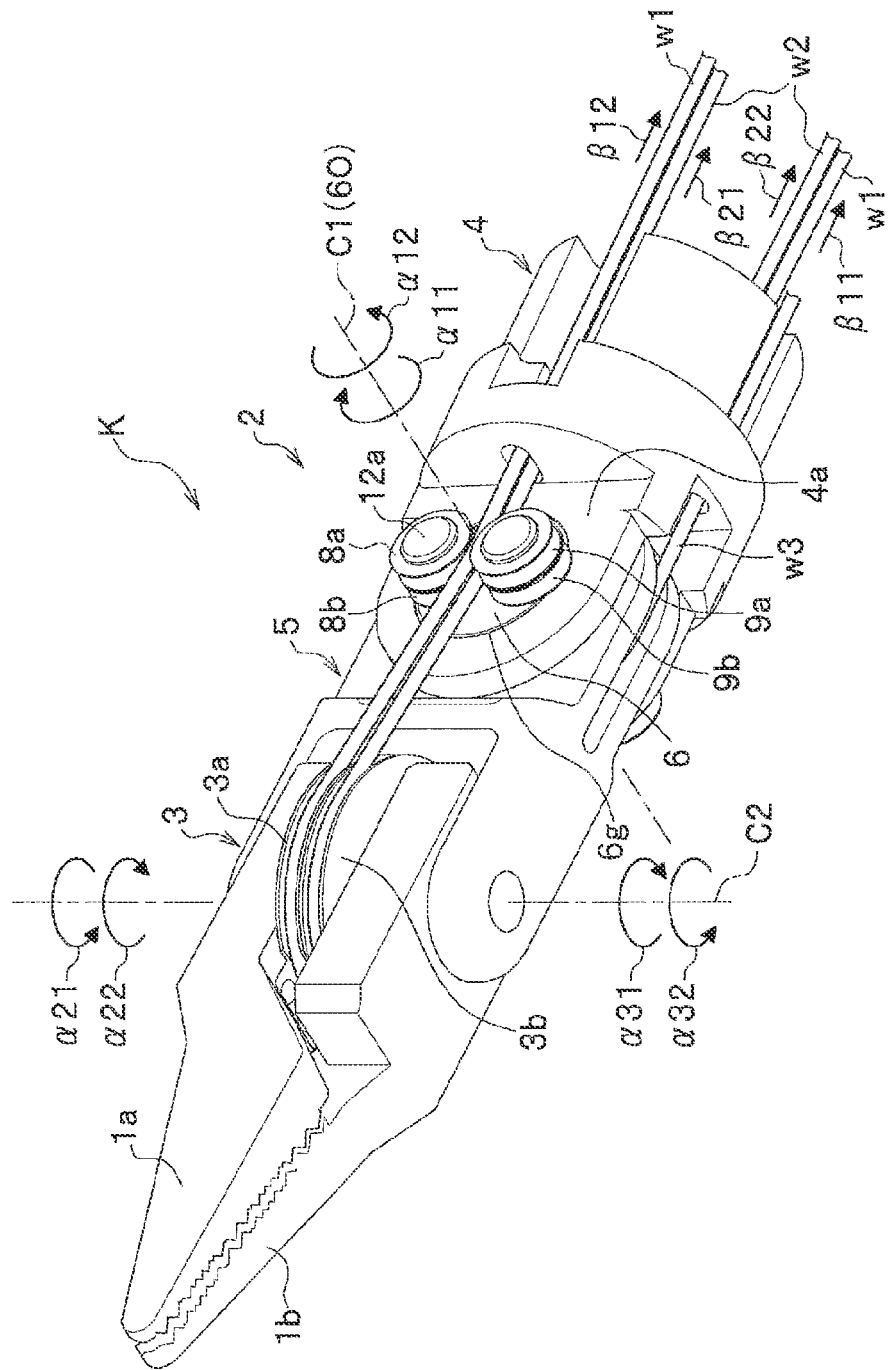
FIG. 7 illustrates the forceps device as viewed in a direction of an arrow A in FIG. 6.
Figure 8:
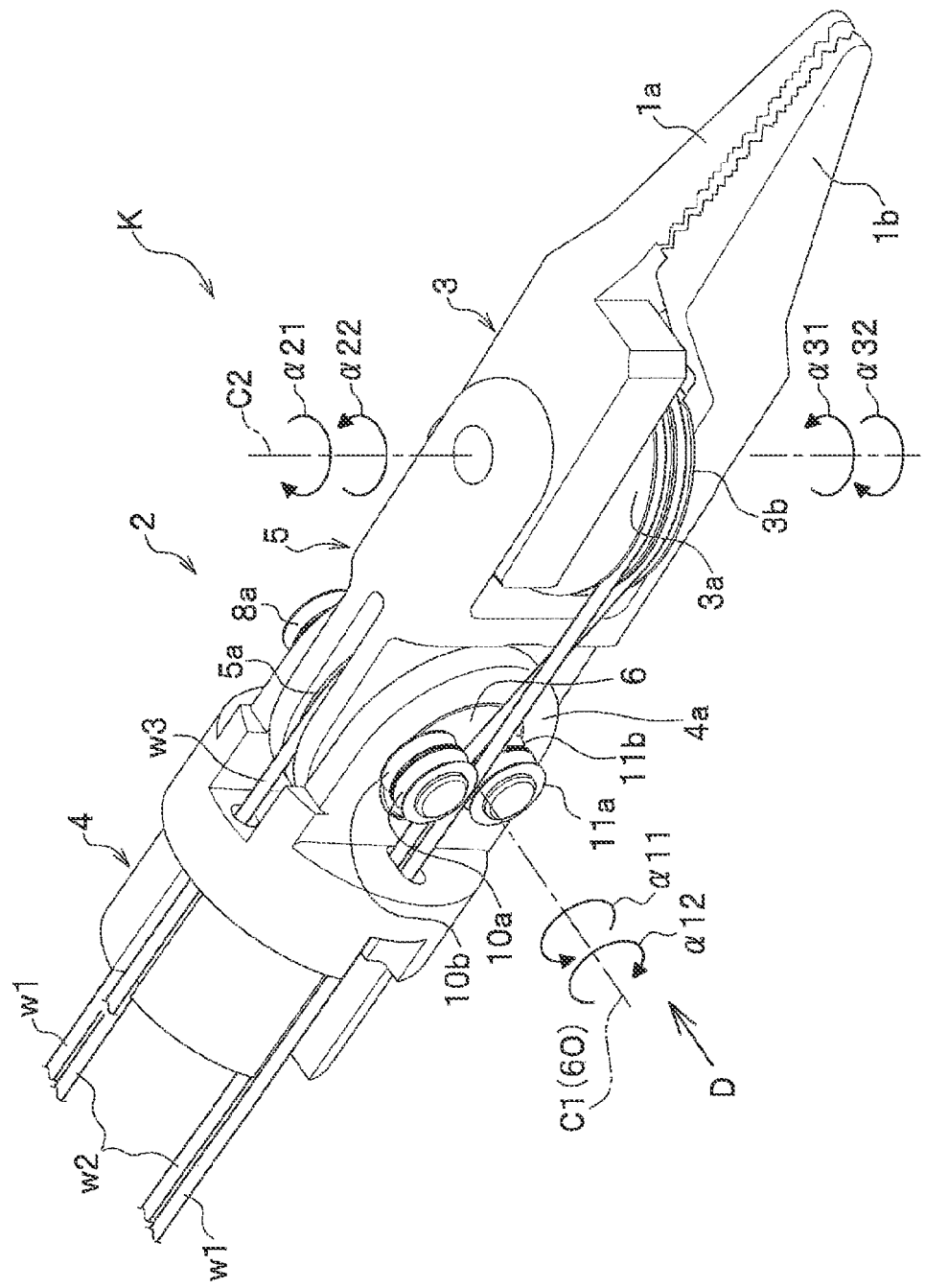
FIG. 8 illustrates the forceps device as viewed in a direction of an arrow B in FIG. 6.
Figure 9:
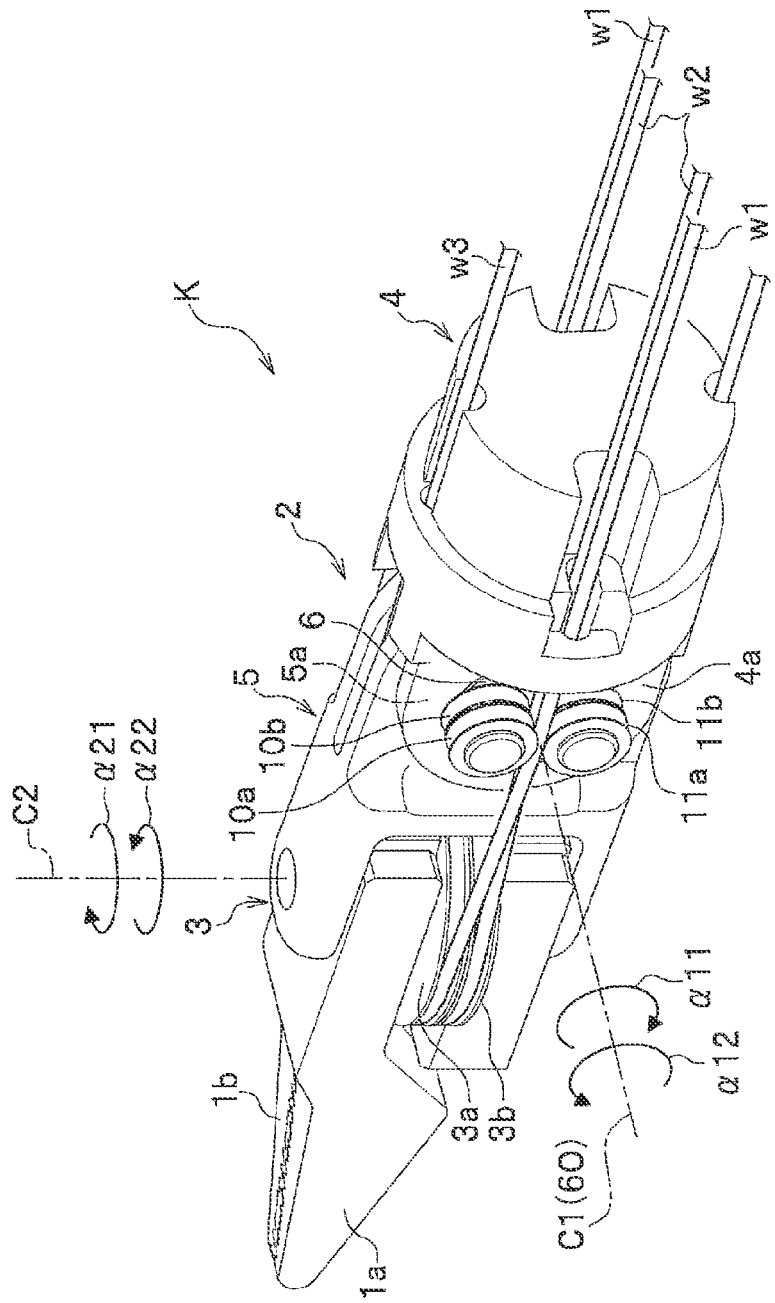
FIG. 9 illustrates the forceps device as viewed in a direction of an arrow C in FIG. 6.

FIG. 6 is a perspective view of the forceps device K according to an embodiment. FIG. 7 illustrates the forceps device K according to the embodiment as viewed in the direction of an arrow A in FIG. 6. FIG. 8 illustrates the forceps device K according to the embodiment as viewed in the direction of an arrow B in FIG. 6. FIG. 9 illustrates the forceps device K according to the embodiment as viewed in the direction of an arrow C in FIG. 6. The forceps device K according to an embodiment includes a pair of grasping portions 1a and 1b on the leading end side thereof, a first joint 2 on the base side thereof, and a second joint 3 therebetween.

The pair of grasping portions 1a and 1b has a function of pinching and releasing an object. The first joint 2 is a junction of a first arm 4 on the base side and a second arm 5 at a middle position, and allows bending of the first arm 4 and the second arm 5 relative to each other. In other words, the first arm 4 and the second arm 5 bend about the rotation center C1 of the first joint 2 (arrows $\alpha 11$ and $\alpha 12$ in FIGS. 6 and 7).

Thus, a second arm pulley 5a formed at one end of the second arm 5 is supported to be turnable about the rotation center C1 by a connecting portion 4a at one end of the first arm 4 on the base side. A third wire w3 for turning the second arm 5 about the rotation center C1 is passed over the second arm pulley 5a integrated with the second arm 5. Because the second arm pulley 5a is supported to be turnable about the rotation center C1, the relation between the moving length of the third wire w3 and the turning angle of the second arm 5 may be kept constant.

The second joint 3 turns each of the grasping portion 1a and the grasping portion 1b relative to the second arm 5 about a rotation center C2 to grasp and release an object. Specifically, the grasping portion 1a is turned about the rotation center C2 (arrows $\alpha 21$ and $\alpha 22$ in FIGS. 6 and 7), and the grasping portion 1b is turned about the rotation center C2 (arrows $\alpha 31$ and $\alpha 32$ in FIG. 6).

Thus, a first pulley 3a is formed integrally with the grasping portion 1a. The grasping portion 1a and the first pulley 3a are supported to be turnable about the rotation center C2. In addition, a second pulley 3b is formed integrally with the grasping portion 1b. The grasping portion 1b and the second pulley 3b are supported to be turnable about the rotation center C2.

For pinching an object with the grasping portion 1a and the grasping portion 1b, the grasping portion 1a is turned in the direction of the arrow $\alpha 21$ and the grasping portion 1b is turned in the direction of the arrow $\alpha 31$. In contrast, for releasing the grasping portion 1a and the grasping portion 1b from a state in which an object is pinched, the grasping portion 1a is turned in the direction of the arrow α22 and the grasping portion 1b is turned in the direction of the arrow α32.

A first wire w1 for turning the first pulley 3a in the directions of the arrows α21 and α22 in FIGS. 6 and 7 is therefore passed over the first pulley 3a. In addition, a second wire w2 for turning the second pulley 3b in the directions of the arrows α31 and α32 in FIG. 6 is passed over the second pulley 3b. A roller base 6 having a columnar shape is rotatably supported by the connecting portion 4a, which constitutes the first joint 2, of the first arm 4.

The roller base 6 rotatably supports a first guide roller 8a, a second guide roller 9a, a third guide roller 10a, and a fourth guide roller 11a for guiding the first wire w1. In addition, the roller base 6 rotatably supports a first guide roller 8b, a second guide roller 9b, a third guide roller 10b, and a fourth guide roller 11b for guiding the second wire w2.

The outer circumferential face 6g of the roller base 6 slides relative to the connecting portion 4a of the first arm 4, so that the roller base 6 is supported to be rotatable about the rotation center C1 of the first joint 2 or about the vicinity of the rotation center C1. In other words, the roller base 6 may perform rotational movement independently of the movements of the first arm 4, the second arm 5, and the first joint 2.

The first guide rollers 8a and 8b and the second guide rollers 9a and 9b are rotatably supported on one base side of the columnar roller base 6. As illustrated in FIGS. 8 and 9, the third guide rollers 10a and 10b and the fourth guide rollers 11a and 11b are rotatably supported on the other base side of the roller base 6.

Note that the center 10O around which the first wire w1 and the second wire w2 are guided between the guide rollers (8 and 9) and/or around which the first wire w1 and the second wire w2 are guided between the guide rollers (10 and 11) (FIGS. 11A and 11B) is coincident or substantially coincident with the rotation center 6O of the roller base 6. This configuration enables prevention or reduction of a change in the path lengths of the wires (w1 and w2).

Roller Base 6 and First to Fourth Guide Rollers 8 to 11

Figure 10:
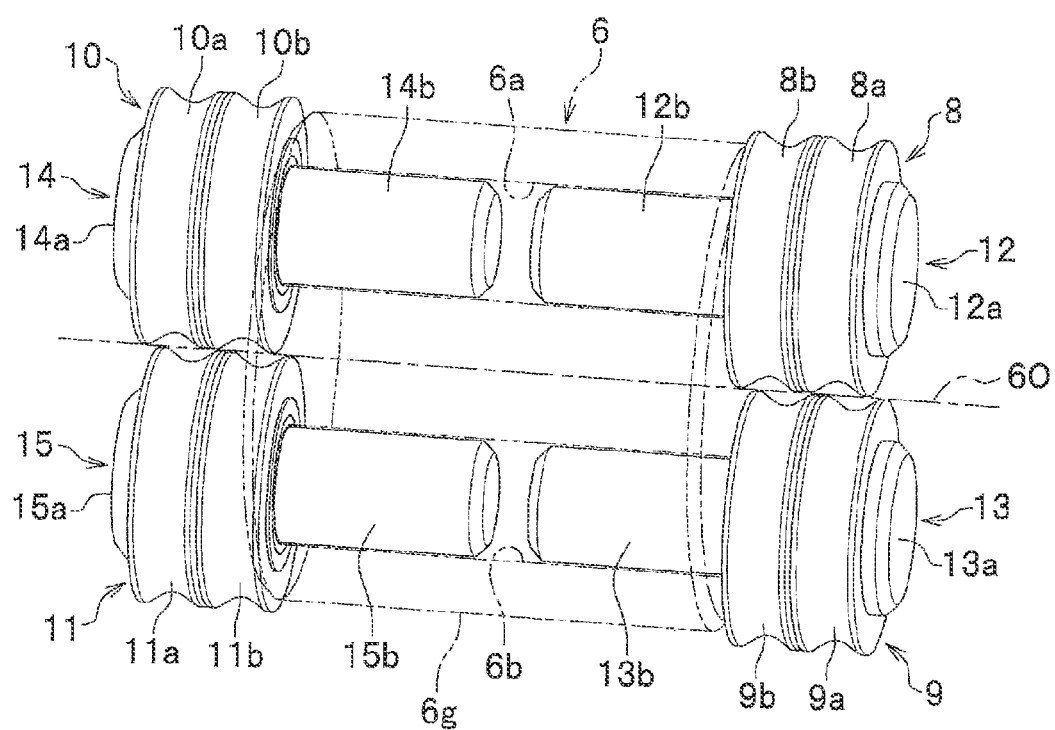
FIG. 10 is a perspective view illustrating a roller base and first to fourth guide rollers, according to an embodiment.

FIG. 10 is a perspective view illustrating the roller base 6 and the first to fourth guide rollers 8 to 11. The roller base 6 is formed of metal, resin, or the like into a columnar shape. The roller base 6 has a first insertion hole 6a and second insertion hole 6b formed therethrough along its axial direction. The first insertion hole 6a is a hole for arranging the first guide rollers 8 (8a and 8b) and the third guide rollers 10 (10a and 10b). The second insertion hole 6b is a hole for arranging the second and fourth guide rollers 9 (9a and 9b) and 11 (11a and 11b). For the guide rollers (8a to 11b), stainless steel is used, for example. Alternatively, the guide rollers (8a to 11b) may be made of other metal, resin, or the like as long as the material meets such conditions as friction, weatherability, and sterilization.

A shaft part 12b of a first support shaft 12 is inserted in the first insertion hole 6a through the first guide rollers 8a and 8b and fixed therein by press-fitting or the like. The first support shaft 12 has the shaft part 12b and a head part 12a having a larger diameter. The first guide rollers 8a and 8b, through which the shaft part 12b of the first support shaft 12 is inserted, are rotatably supported by the first support shaft 12. The first guide rollers 8a and 8b are arranged between the roller base 6 and the head part 12a of the first support shaft 12.

In addition, a shaft part 14b of a third support shaft 14 is inserted in the opposite side of the first insertion hole 6a through the third guide rollers 10a and 10b and fixed therein by press-fitting or the like. The third support shaft 14 has the shaft part 14b and a head part 14a having a larger diameter. The third guide rollers 10a and 10b, through which the shaft part 14b of the third support shaft 14 is inserted, are rotatably supported by the third support shaft 14. The third guide rollers 10a and 10b are arranged between the roller base 6 and the head part 14a of the third support shaft 14.

A shaft part 13b of a second support shaft 13 is inserted in the second insertion hole 6b through the second guide rollers 9a and 9b and fixed therein by press-fitting or the like. The second support shaft 13 has the shaft part 13b and a head part 13a having a larger diameter. The second guide rollers 9a and 9b, through which the shaft part 13b of the second support shaft 13 is inserted, are rotatably supported by the second support shaft 13. The second guide rollers 9a and 9b are arranged between the roller base 6 and the head part 13a of the second support shaft 13.

In addition, a shaft part 15b of a fourth support shaft 15 is inserted in the opposite side of the second insertion hole 6b through the fourth guide rollers 11a and 11b and fixed therein by press-fitting or the like. The fourth support shaft 15 has the shaft part 15b and a head part 15a having a larger diameter. The fourth guide rollers 11a and 11b, through which the shaft part 15b of the fourth support shaft 15 is inserted, are rotatably supported by the fourth support shaft 15. The fourth guide rollers 11a and 11b are arranged between the roller base 6 and the head part 15a of the fourth support shaft 15.

As illustrated in FIG. 6, the first wire w1 is passed between the first guide roller 8a and the second guide roller 9a. The first wire w1 is then passed over the first pulley 3a and, as illustrated in FIG. 8, guided between the third guide roller 10a and the fourth guide roller 11a, which are rotatably supported on the other side of the roller base 6.

As illustrated in FIG. 7, the second wire w2 is passed between the first guide roller 8b and the second guide roller 9b. The second wire w2 is then passed over the second pulley 3b and, as illustrated in FIG. 9, guided between the third guide roller 10b and the fourth guide roller 11b, which are rotatably supported on the other side of the roller base 6. The first wire w1 and the second wire w2 are arranged to pass the rotation center C1 of the first joint 2 or the vicinity thereof.

Bending Movement at First Joint 2 of Forceps Device K

Figure 11A:
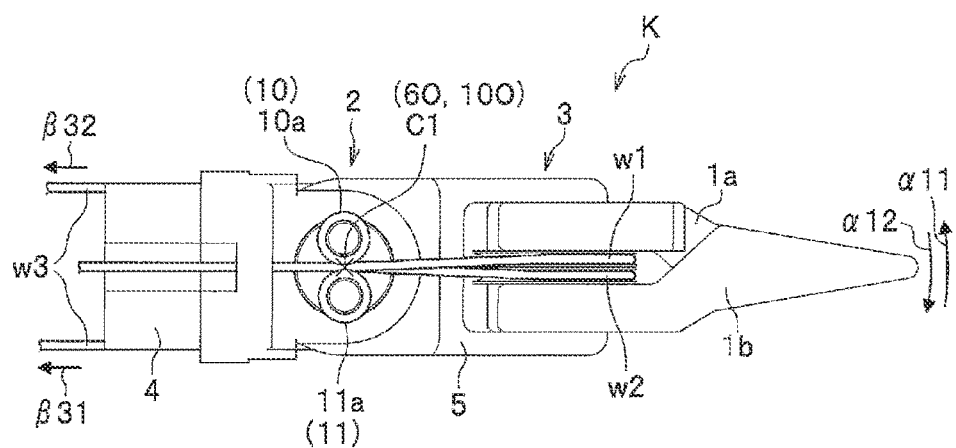
FIG. 11A is a view in a direction D in FIG. 8.

With the structure as described above, the forceps device K performs a first bending movement as described below. FIG. 11A is a view in a direction D in FIG. 8, and FIG. 11B illustrates a state in which the first joint 2 is bending from a state illustrated in FIG. 11A.

Figure 11B:
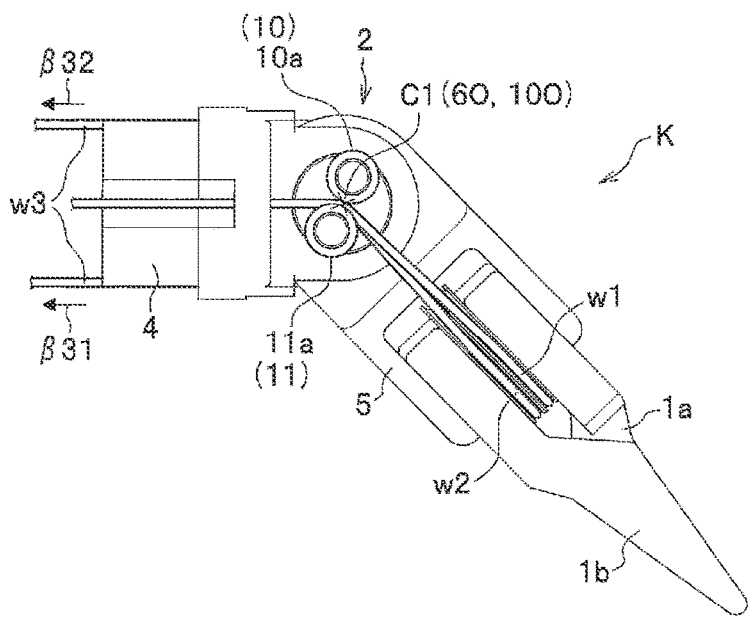
FIG. 11B illustrates a state in which a first joint is bending from a state illustrated in FIG. 11A, according to an embodiment.

In the forceps device K, when the third wire w3 is pulled in a direction β31 in FIG. 11A from the state in FIG. 11A, the second arm pulley 5a turns about the rotation center C1, which turns the second arm 5 about the rotation center C1 relative to the first arm 4 (in the direction of an arrow α12 in FIG. 11A) as illustrated in FIG. 11B.

In contrast, in the forceps device K, when the third wire w3 is pulled in a direction β32 in FIG. 11A from the state in FIG. 11A, the second arm pulley 5a turns about the rotation center C1, which turns the second arm 5 about the rotation center C1 relative to the first arm 4 in a direction opposite the direction in which the second arm 5 is turned in FIG. 11B (in the direction of an arrow α11 in FIG. 11A).

Grasping Movement at Second Joint 3 of Forceps Device K

For pinching an object with the grasping portions 1a and 1b, the first wire w1 is moved in a direction of an arrow β11, so that the first pulley 3a and the grasping portion 1a are turned about the rotation center C2 in the direction of the arrow α21 as illustrated in FIG. 6. In addition, the second wire w2 is moved in the direction of an arrow β21, so that the second pulley 3b and the grasping portion 1b are turned about the rotation center C2 in the direction of the arrow α31.

In contrast, for releasing an object pinched with the grasping portion 1a and the grasping portion 1b, the first wire w1 is moved in a direction of an arrow β12, so that the first pulley 3a and the grasping portion 1a are turned about the rotation center C2 in the direction of the arrow α22 as illustrated in FIG. 6. In addition, the second wire w2 is moved in a direction of an arrow β22, so that the second pulley 3b and the grasping portion 1b are turned about the rotation center C2 in the direction of the arrow α32.

Bending Movement at Second Joint 3 of Forceps Device K

With the structure as described above, the forceps device K performs a second bending movement as described below. For bending the grasping portions 1a and 1b at the same time in one direction, the first wire w1 is moved in the direction of the arrow β11, so that the first pulley 3a and the grasping portion 1a are turned about the rotation center C2 in the direction of the arrow α21 as illustrated in FIG. 6. In addition, the second wire w2 is moved in the direction of the arrow β22, so that the second pulley 3b and the grasping portion 1b are turned about the rotation center C2 in the direction of the arrow α32. In this manner, at the second joint 3, the entire grasping portions 1a and 1b may be bent about the rotation center C2 in the direction of the arrow α21 (the direction of the arrow α32).

In contrast, for bending the grasping portions 1a and 1b at the same time in the other direction, the first wire w1 is moved in the direction of the arrow β12, so that the first pulley 3a and the grasping portion 1a are turned about the rotation center C2 in the direction of the arrow α22 as illustrated in FIG. 6. In addition, the second wire w2 is moved in the direction of the arrow β21, so that the second pulley 3b and the grasping portion 1b are turned about the rotation center C2 in the direction of the arrow α31. In this manner, at the second joint 3, the entire grasping portions 1a and 1b may be bent about the rotation center C2 in the direction of the arrow α22 (the direction of the arrow α31).

Relation Between Wires w1, w2, and w3 in Forceps Device K and Wires 35a, 35b, and 35c in Housing 20

In the forceps device, three wires w1, w2, and w3 are used, which have different roles. For example, the first wire w1 corresponds to extension of the wire 35a in the housing 20 through the shaft 111, the second wire w2 corresponds to extension of the wire 35c in the housing 20 through the shaft 111, and the third wire w3 corresponds to extension of the wire 35b in the housing 20 through the shaft 111.

The driving force from the power unit 104, in which pistons like pneumatic actuators linearly move, linearly moves the drive elements 31 in the housing 20. As a result, the wires are pulled in predetermined directions, which allows the bending movements of the forceps device and the opening and closing movements of the grasping portions thereof. In the surgical device 100 according to an embodiment, the movements of individual components of the forceps device K are controlled via the three wires (three braided wires).

Operations and Effects (1) The surgical device 100 according to an embodiment includes the forceps device K capable of performing bending movements, and opening and closing movements of the grasping portions thereof, a plurality of drive elements 31a, 31b, and 31c to which driving force is transmitted from outside, and a plurality of wires 35a, 35b, and 35c fixed to the drive elements 31a, 31b, and 31c, respectively, to transmit linear movements of the drive elements 31a, 31b, and 31c to the forceps device K. The forceps device K is structured to perform at least any of the bending movements and the opening and closing movements when all or some of the wires 35a, 35b, and 35c are pulled.

Thus, linear movements of the drive elements 31a, 31b, and 31c are transmitted to the forceps device K via the wires 35a (and the first wire w1), 35b (and the third wire w3), and 35c (and the second wire w2), and all or some of the wires 35a, 35b, and 35c are pulled, which enables at least any of the bending movements and the opening and closing movements. In addition, because the movements of the drive elements 31a, 31b, and 31c transmitted by the wires 35a, 35b, and 35c are linear, the structure of the drive elements 31a, 31b, and 31c may be made simple.

In addition, a plurality of driven portions according to an embodiment are the drive element 31a, the drive element 31b, and the drive element 31c. A plurality of cords according to an embodiment are the wire 35a fixed to the drive element 31a, the wire 35b fixed to the drive element 31b, and the wire 35c fixed to the drive element 31c. Thus, the movements of the drive elements 31a, 31b, and 31c may be individually controlled, which enables the bending movements and the opening and closing movements of the forceps device K to be controlled independently of each other.

The drive elements 31a, 31b, and 31c each linearly move in the first direction (the Z direction in FIG. 4), that is, in parallel with each other, and are arranged in a second direction (the X direction in FIG. 4) intersecting the first direction. This prevents the linear movement of each of the drive elements 31a, 31b, and 31c from interfering with the movements of the other drive elements. In addition, the arrangement of the drive elements 31a, 31b, and 31c in the second direction facilitates the layout of the drive elements 31a, 31b, and 31c.

The forceps device K is structured to perform the first bending movement (turning about the rotation center C1), the second bending movement (turning about the rotation center C2) in a direction different from the first bending movement, and the opening and closing movements (opening and closing of the grasping portions 1a and 1b about the rotation center C2) by the movements of the first wire w1, the second wire w2, and the third wire w3. As a result, complicated movements of the forceps device K may be achieved by linear movements of a plurality of wires.

The forceps device K is structured such that the movements of the first wire w1 and the second wire w2 cause the second bending movement (turning about the rotation center C2) and the opening and closing movements (opening and closing of the grasping portions 1a and 1b about the rotation center C2), and the movement of the third wire w3 causes the first bending movement (turning about the rotation center C2).

Note that the technical scope of the present disclosure is not limited to the embodiment described above, and various modifications may be made without departing from spirit and scope of the appended claims.

For example, in an embodiment described above, the first wire w1 corresponds to extension of the wire 35a through the shaft 111, the second wire w2 corresponds to extension of the wire 35c through the shaft 111, and the third wire w3 corresponds to extension of the wire 35b through the shaft 111. Alternatively, the second wire w2 may correspond to extension of the wire 35b, and the third wire w3 may be extension of the wire 35c.

In addition, in an embodiment described above, cooperation of the first wire w1 and the second wire w2 achieves the second bending movement in a direction different from the first bending movement and the grasping movement (opening and closing movements) of the grasping portions at the leading end of the forceps. Alternatively, the forceps device K may be structured such that one of the first wire w1 and the second wire w2 causes the second bending movement and the other causes the grasping movement. In addition, the correspondence between the wires w1, w2, and w3 in the forceps device K and the wires 35a, 35b, and 35c in the housing 20 may be different from the combinations in the various embodiments described above.

What is claimed is:

1. A surgical device comprising:
   a forceps device configured to perform a bending movement and to perform opening and closing movements of grasping portions of the forceps device;
   a plurality of driven portions to which a driving force is transmitted from outside the surgical device; and
   a plurality of cords, each being fixed to one of the plurality of driven portions, the plurality of cords transmitting movements of the plurality of driven portions to the forceps device,
   wherein the forceps device performs at least one of the bending movement and the opening and closing movements when at least a portion of the plurality of cords are pulled,
   wherein the plurality of driven portions include a first driven portion, a second driven portion, and a third driven portion,
   wherein the plurality of cords include a first wire fixed to the first driven portion, a second wire fixed to the second driven portion, and a third wire fixed to the third driven portion, and
   wherein the first driven portion, the second driven portion, and the third driven portion linearly move in parallel with each other in a first direction, and are arranged in a second direction that intersects the first direction.

2. The surgical device according to claim 1, wherein the forceps device performs:
   a first bending movement;
   a second bending movement in a direction different from a direction of the first bending movement; and
   the opening and closing movements, and
   wherein the first bending movement, the second bending movement, and the opening and closing movements are caused by movements of the first wire, the second wire, and the third wire, respectively.

3. The surgical device according to claim 1, wherein the forceps device performs:
   a first bending movement;
   a second bending movement in a direction different from a direction of the first bending movement; and
   the opening and closing movements, and
   wherein the first bending movement, the second bending movement, and the opening and closing movements are caused by movements of the first wire, the second wire, and the third wire.

4. The surgical device according to claim 2, wherein the forceps device performs:
   the second bending movement and the opening and closing movements caused by the movements of the first wire and the second wire; and
   the first bending movement caused by the movement of the third wire.

5. The surgical device according to claim 3, wherein the forceps device performs:
   the second bending movement and the opening and closing movements caused by the movements of the first wire and the second wire; and
   the first bending movement caused by the movement of the third wire.

6. The surgical device according to claim 1, wherein the forceps device performs at least one of the bending movement and the opening and closing movements when all of the plurality of cords are pulled.

7. The surgical device according to claim 1, wherein the forceps device performs the bending movement when all of the plurality of cords are pulled.

8. The surgical device according to claim 1, wherein the forceps device performs the opening and closing movements when all of the plurality of cords are pulled.

9. The surgical device according to claim 1, wherein the forceps device simultaneously performs the bending movement and the opening and closing movements when a portion of the plurality of cords are pulled.

10. The surgical device according to claim 1, wherein the forceps device simultaneously performs the bending movement and the opening and closing movements when all of the plurality of cords are pulled.

11. The surgical device according to claim 1, wherein the forceps device comprises:
    a first arm;
    a second arm comprising a second arm pulley, the second arm configured to rotate with respect to the first arm about a first axis with rotation of the second arm pulley; and
    a plurality of grasping portions, each comprising a pulley, the plurality of grasping portions configured to rotate with respect to the second arm about a second axis with rotation of the pulleys, the second axis being different than the first axis, and
    wherein the plurality of cords are configured to rotate the second arm pulley and the pulleys of the grasping portions.

12. The surgical device according to claim 11, wherein the second arm comprises a connecting portion that rotatably connects to the first arm,
    wherein the connecting portion rotatably supports a roller base comprising a plurality of guide rollers, and wherein first cords of the plurality of cords are configured to rotate the pulleys of the plurality of grasping portions, and a second cord of the plurality of cords is configured to rotate the second arm pulley, and the first cords pass through the plurality of guide rollers.

13. The surgical device according to claim 1, wherein the forceps device comprises a first joint rotatable about a first axis and a second joint rotatable about a second axis that is different from the first axis, and wherein the first joint is configured to rotate independently of a rotation of the second joint.

14. The surgical device according to claim 13, wherein the first joint generates the bending movement and the second joint generates the opening and closing movements.

* * * * *